United States Patent [19]

Terashima et al.

[11] Patent Number: 5,286,624
[45] Date of Patent: Feb. 15, 1994

[54] INTEGRAL MULTILAYER ANALYTICAL ELEMENT FOR DETERMINATION OF AMMONIA OR AMMONIA-PRODUCING SUBSTANCE

[75] Inventors: Kaoru Terashima; Toru Kitani; Toshihiro Mori; Tsuneo Kawase, all of Saitama, Japan

[73] Assignee: Fuji Photo Film Co., Ltd., Kanagawa, Japan

[21] Appl. No.: 779,363

[22] Filed: Oct. 17, 1991

[30] Foreign Application Priority Data

Oct. 19, 1990 [JP] Japan ................... 2-281087

[51] Int. Cl.$^5$ .................... C12Q 1/58; C12Q 1/50; G01N 21/77
[52] U.S. Cl. ......................... 435/12; 435/17; 435/805; 422/56; 422/57; 436/169; 436/170; 526/332
[58] Field of Search ............... 435/12, 17, 805; 422/56, 57; 436/169, 170; 526/332

[56] References Cited

U.S. PATENT DOCUMENTS

| | | | |
|---|---|---|---|
| 2,799,669 | 7/1957 | Zoss | 526/332 |
| 4,557,901 | 12/1985 | Koyama | 422/56 |
| 4,604,347 | 8/1986 | Arai | 435/4 |
| 4,895,704 | 1/1990 | Arai | 422/57 |

FOREIGN PATENT DOCUMENTS

0204334 12/1986 European Pat. Off. .
0287112 10/1988 European Pat. Off. .

OTHER PUBLICATIONS

Encyclopedia of Polymer Science & Engineering vol. 17, John Wiley & Sons N.Y. 1989, pp. 456–457.

*Primary Examiner*—Michael G. Wityshyn
*Assistant Examiner*—Ralph Gitomer
*Attorney, Agent, or Firm*—McAulay Fisher Nissen Goldberg & Kiel

[57] ABSTRACT

An integral multilayer analytical element for the determination of ammonia or an ammonia-producing substance comprising a light-transmissive liquid-impermeable support, an indicator layer containing an indicator which produces a detectable change by gaseous ammonia, a liquid permeation barrier layer, a reagent layer containing an alkaline buffer and optionally a reagent capable of reacting with a substance to produce ammonia and a spreading layer laminated in this order, which is improved by that the indicator layer contains a polyvinyl alkyl ether, and/or which is improved by that the surface of said support facing toward the indicator layer is undercoated with a polyvinyl alkyl ether, a hydroxyalkyl cellulose, an alkyl cellulose, polystyrene, a polyalkyl methacrylate, polyviriylidene chloride, polyvinyl alcohol or polyvinyl pyrrolidone, substantially not containing ammonia and ammonium ion. By using the above analytical element, ammonia or an ammonia-producing substance can be analyzed at a high coloring optical density and a high accuracy. The measuring accuracy is further improved by lowering the background optical density.

14 Claims, No Drawings

INTEGRAL MULTILAYER ANALYTICAL ELEMENT FOR DETERMINATION OF AMMONIA OR AMMONIA-PRODUCING SUBSTANCE

BACKGROUND OF THE INVENTION

This invention relates to an integral multilayer analytical element for the determination of ammonia or an ammonia-producing substance in a liquid sample. More particularly, this invention relates to an integral multilayer analytical element suitable for the determination of ammonia or an ammonia-producing substance such as creatinine or urea contained in a biological body fluid such as blood, urine or lymph.

The quantitative analysis of ammonia, creatinine, urea or the like is very important for the diagnosis of various diseases such as nephropathy, the inspection for the medical treatment course of the disease, and the inspection of renal functions.

A representative analytical method for an ammonia-producing substance comprises a process for producing ammonia from the ammonia-producing substance and a process for determining the produced ammonia. The analytical method of utilizing the conversion to ammonia has been widely utilized in the so-called wet analysis or the solution method. Recently, in the dry analysis using a dry analytical device represented by integral multilayer analytical elements, the analytical method of utilizing the conversion to ammonia has been applied or proposed.

As the process for producing ammonia from an ammonia-producing substance, a common method is of producing ammonia by the action of an enzyme. For example, creatinine in a biological body fluid is determined by utilizing creatinine deiminase (EC 3.5.4.21) which hydrolzes specifically creatinine in the body fluid to ammonia and N-methylhydantion. Urea nitrogen (BUN) in a biological body fluid is determined by utilizing urease which hydrolyzes urea to ammonia and carbon dioxide. In the above methods, since the ammonia-producing substance, which is an analyte, is a substrate of an enzyme, the substance is called also ammonia-producing substrate. Analytical methods of the ammonia-producing substance are described in various references, such as "Analytical Chemistry", 46, 246 (1974), "Climica Clinica Acta", 18, 409 (1967), "Rinsho Kagaku Bunseki III Gan-Chisso Seibun (Clinical Chemical Analysis III Nitrogen-Containing Components) 2nd Edition", Tokyo Kagaku Dojin, Tokyo, 13–14, 67–87 (1979) and "Rinsho Kensa (Journal of Medical Technology)" 5(6), 387–391 (1961).

Integral analytical elements usable for the analysis of ammonia or an ammonia-producing substrate are the integral multilayer analytical element described in Japanese Patent KOKOKU No. 58(1983)-19062 (U.S. Pat. No. Reissue No. 30,267), the integral multilayer analytical elements for the analysis of ammonia or an ammonia-producing substrate disclosed in U.S. Pat. No. 4,548,906 (Japanese Patent KOKAI No. 58(1983)-77661) and Japanese Patent KOKAI No. 58(1983)-77660 and the like. The fundamental construction of the above analytical elements is composed of a light-transmissive, liquid-impermeable support, an ammonia indicator layer containing an indicator which produces a detectable change by contacting ammonia, a liquid permeation barrier layer which is permeable to gaseous ammonia and substantially impermeable to liquid, a reaction layer containing a reagent which reacts with an ammonia-producing substrate to produce ammonia and a porous spreading layer laminated in this order. The integral multilayer analytical element disclosed in EP 0 204 334 A has a trapping function of the ammonia contained in a body fluid (endogeneous ammonia) in the analytical element itself, and the analytical element can remove the influence of the endogeneous ammonia. This analytical element is provided with an endogeneous ammonia-trapping layer which conducts an ammonia-trapping reaction above the layer generating ammonia through an ammonia-producing reaction in contact therewith. The integral multilayer analytical element disclosed in EP 0 287 112 A is provided with a layer having a diffusion-preventing ability which does not perform trapping of ammonia and ammonia-producing reaction between the endogeneous ammonia-trapping layer and the ammonia-producing reaction reagent layer.

Heretofore, a copolymer latex of polyvinyl acetate-acrylate ester was used as the binder of the indicator layer. However, the analytical element using the above copolymer latex is insufficient in sensitivity, and the accuracy (CV=variation coefficient) is inferior. Since the coating solution is latex, it is inferior in the liquid stability because of the occurrence of precipitation. Moreover, since a pH variation of the latex solution occurs, this analytical element is unsuitable for the system using a pH indiator.

SUMMARY OF THE INVENTION

An object of the invention is to provide an integral multilayer analytical element for the determination of ammonia or an ammonia-producing substance of which the developed color density is higher and the measuring accuracy is higher.

Another object of the invention is to provide an integral multilayer analytical element for the determination of ammonia or an ammonia-producing substance of which the background color density is low and the measuring accuracy is thereby further improved.

The present invention has achieved the above objects, and provided an integral multilayer analytical element for the determination of ammonia or an ammonia-producing substance comprising a light-transmissive liquid-impermeable support, an indicator layer containing an indicator which produces a detectable change by gaseous ammonia, a liquid permeation barrier layer, a reagent layer containing an alkaline buffer and optionally a reagent capable of reacting with a substrate to produce ammonia and a spreading layer laminated in this order, which is improved in that the indicator layer contains a polyvinyl alkyl ether.

The present invention also provides an integral multilayer analytical element for the determination of ammonia or an ammonia-producing substance comprising a light-transmissive liquid-impermeable support, an indicator layer containing an indicator which produces a detectable change by gaseous ammonia, a liquid permeation barrier layer, a reagent layer containing an alkaline buffer and optionally a reagent capable of reacting with a substrate to produce ammonia and a spreading layer laminated in this order, which is improved in that the surface of said support on the indicator layer side is undercoated with a polyvinyl alkyl ether, a hydroxyalkyl cellulose, an alkyl cellulose, polystyrene, a polyalkyl methacrylate, polyvinylidene chloride, polyvinyl alcohol or polyvinyl pyrrolidone, substantially not containing ammonia and ammonium ion.

DETAILED DESCRIPTION OF THE INVENTION

The light-transmissive liquid-impermeable suport is composed of polyethylene terephthalate, polycarbonate of bisphenol A, polystyrene, cellulose ester (for example, cellulose diacetate, cellulose triacetate or cellulose acetate propionate, etc.), and the thickness is in the range of about 50 $\mu$m to about 1 mm, preferably about 80 $\mu$m to about 300 $\mu$m.

An undercoat layer containig a particular polymer can be provided on the surface of the support in order to render the adhesion of the indicator layer to the support tight. The analytical element of the invention is characterized by using a polyvinyl alkyl ether, a hydroxyalkyl cellulose, an alkyl cellulose, polystyrene, a polyalkyl methacrylate, polyvinylidene chloride, polyvinyl alcohol or polyvinyl pyrrolidone, substantially not containing ammonia and ammonium ion, instead of gelatin as the undercoat layer. The polyvinyl alkyl ether is polyvinyl methyl ether, polyvinyl ethyl ether, polyvinyl isobutyl ether or the like, and the hydroxyalkyl cellulose is hydroxymethyl cellulose, hydroxyethyl cellulose. The alkyl cellulose is methyl cellulose, ethyl cellulose or the like. Among them, the polyvinyl alkyl ethers are the most preferred.

The undercoat layer is composed of the above polymer and an anchoring agent which is optionally added. As the anchoring agent, an organic solvent which allows swelling or dissolves the support can be used. In the case where the support is polyethylene terephthalate, suitable anchoring agents are phenol, phenol deriatives, such as, o-chlorophenol, p-chlorophenol and cresol, 2-nitropropanol, acetonylacetone, acetophenone, etc. The undercoat layer can be provided by dissolving the polymer and the anchoring agent in a solvent, such as, methanol, ethanol, methyl cellosolve (B-hydroxyethylmethyl ether) or acetone in a polymer concentration of about 0.1% to about 2%, preferably about 0.1% to about 1%, applying the above undercoating solution by a known method followed by drying. The coating amount of the polymer is usually about 5 mg/m$^2$ to about 500 mg/m$^2$, preferably about 10 mg/m$^2$ to about 300 mg/m$^2$. The ratio of the polymer to the anchoring agent is about 1:10 to about 1:100 by weight.

Prior to applying the undercoating solution, the surface of the support may be provided with a physical activation treatment, such as, glow discharge or ultraviolet irradiation, or a chemical activation treatment.

The indicator layer (ammonia indicator layer) containing an indicator which produces a detectable change by gaseous ammonia is provided on the support directly or through the undercoat layer. The indicator layer contains at least one kind of coloring ammonia indicator. The coloring ammonia indicator is a compound which produces a detectable change, such as, coloring or color change due to the change of absorption wave length, by gaseous ammonia.

The coloring ammonia indicator usable for the integral multilayer analytical element of the invention includes leuco dyes, such as, leuco cyanine dye, nitro-substituted leuco dye, and leuco phthalein dye,,disclosed in U.S. Pat. No. Reissue No. 30 267 or Japanese Patent KOKOKU No. 58-19062, pH indicators, such as, Bromophenol Blue, Bromocresol Green, Bromthymol Blue, Quinoline Blue and rosolic acid disclosed in "Kagaku Dai Jiten, Encyclopaedia Chimica", vol. 10, pp 63–65, Kyoritsu Shuppan, Tokyo, 1962, triarylmethane dye precursors, leuco benzylidene dyes disclosed in Japanese Patent KOKAI No. 55-379 or 56-145273), diazonium salts and azo dye couplers, and alkali-bleachable dyes.

The indicator layer is formed by preparing a coating solution by mixing at least one kind of the coloring ammonia indicator with an organic solvent-soluble binder polymer or a water-soluble binder polymer, and applying the coating solution onto the support followed by drying. Heretofore, the binder polymer used was a cellulose ester, such as, cellulose monoacetate, cellulose diacetate, cellulose triacetate, cellulose acetate butyrate or cellulose propionate, an alkyl cellulose, such as, methyl cellulose, ethyl cellulose or propyl cellulose a synthetic vinyl polymer, such as, polymethyl methacrylate, polyacrylate, polystyrene, polyacrylonitrile, polyvinyl chloride, polyvinyl butyral, chlorinated polyvinyl acetate, polyacrylamide, polyvinyl pyrrolidone or polyvinyl alchol, or a copolymer thereof. The analytical element of the invention is characterized by using a polyvinyl alkyl ether as the binder polymer. Examples of the polyvinyl alkyl ether are polyvinyl methyl ether, polyvinyl ethyl ether, polyvinyl isobutyl ether and the like.

The blending amount of the coloring ammonia indicator is preferably 1 to 20 wt. % of the binder polymer. In order to prevent coloring or discoloration of the coloring ammonia indicator during manufacturing or storing, the pH value at the indicator layer can be controlled to the coloring pH range of the coloring ammonia indicator by adding an organic acid or inorganic acid, such as, ethanesulfonic acid, aspartic acid, azelaic acid, glutaric acid, succinic acid, glutaconic acid, tartaric acid, pimelic acid, malonic acid, malic acid, 3,3-dimethylglutaric acid, citric acid, p-toluenesulfonic acid, perchloric acid or chloric acid or an alkali, such as, sodium hydroxide, potassium hydroxide, disodium carbonate or sodium hydrogen carbonate to the indicator layer.

The coating solution forming the indicator layer can be prepared by adding reagents, such as, the coloring pH to an organic solvent, such as, acetone, 2-methyoxyethanol, methyl ethyl ketone, dichloromethane, dichloroethane, methanol or ethanol or water in a solids concentration of usually about 1 to 30 wt. %, preferably about 3 to 20 wt. The indicator layer can be formed by applying the coating solution onto the support so that the dry thickness becomes usually about 1 to 30 $\mu$m, preferably about 2 to 20 $\mu$m, followed by drying.

The liquid permeation barrier layer (barrier layer) which can pass geseous ammonia is provided on the indicator layer. The barrier layer means that the layer composed of a material which substantially does not pass the liquid components and interfering substances dissolved in the liquid components, such as, alkaline components, of the coating solution and a sample liquid but passes gaseous ammonia through manufacturing the multilayer analytical element, actually at the time of providing the reaction layer described later on the barrier layer by applying and/or through analytical operations.

The barrier layer can be divided into two embodiments in the structural sense. One embodiment is an air barrier layer which is constructed by a porous material having continuous pores wherein an air layer substantially acts as the barrier layer, and the other embodiment is a polymer barrier layer which is a homogeneous nonporous thin layer constructed by a hydrophobic or less hydrophilic polymer.

Examples of the porous material having continuous pores composing the air barrier layer are: a membrane filter, a porous material formed by a fibrous material entangled with, adhered to or bonded to each other, such as, paper, filter paper, felt or nonwoven fabric, a porous material composed of a woven fabric, a knitted fabric or a fine net material.

The membrane filters usable as the air barrier layer are those produced by using a cellulose acetate, such as, cellulose diacetate or cellulose triacetate, cellulose nitrate, regenerated cellulose, polyamide (nylon), polycarbonate of bisphenol A, polyethylene, polyproplyene, a fluorine-containing polymer, such as, polytetrafluoroethylene, or the like. In the case of using the membrane filter for the integral multilayer analytical element of the invention, a suitable thickness is in the range of usually about 30 to 300 μm, preferably 70 to 200 μm. The porosity (void content) of the membrane filter is usually about 25 to 90%, preferably about 60 to 90%. The mean pore size of the membrane filter is in the range of usually about 0.01 to 20 μm, preferably about 0.1 to 10 μm. Membrane filters having the above properties can be prepared according to the method described in U.S. Pat. No. 1,421,341 or U.S. Pat. No. 3,992,158. Besides, various membrane filters are supplied by many manufactures, and the membrane filter can be selected therefrom.

As the porous material formed by a fibrous material entangled with, adhered to or bonded to each other usable as the air barrier layer, there are the porous materials having continuous pores composed of a fibrous material or an aggregate thereof which is physically entangled or physically and/or chemically adhered or bonded, disclosed in Japanese Patent KOKAI No. 58-77660.

Examples of the fibrous material composing the above porous material are natural fibrous materials, such as, cellulose fiber, cotton fiber, hemp fiber, silk fiber and wool fiber, regenerated fibers and semisynthetic fibers, such as, rayon fiber, vinylon fiber and cellulose acetate fiber, synthetic materials, such as, glass fiber, polyethylene fiber, polyethylene terephthalate fiber, polyacrylonitrile fiber and polyvinyl chloride fiber, and fiber materials composed of a mixture of them. As the examples of the porous material produced by using the above fibrous material, there are papers, such as Japanese papers including rice paper(traditional Japanese writing paper), mino paper and shoji paper, filter paper, parchment paper and artificial parchment paper, felt, nonwoven fabric, and the like, made of the fibrous material.

The void content of the porous material formed by a fibrous material entangled with, adhered to or bonded to each other is in the range of usually about 20 to 90%, preferably about 50 to 85%. The mean pore size of the above porous material is in the range of usually about 0.01 to 20 μm, preferably about 0.1 to 10 μm. The thickness of the above porous material is in the range of usually about 50 to 500 μm, preferably about 70 to 300 μm.

As the examples of the woven fabric usable as the air barrier layer, there are various woven fabrics made of a natural fiber, such as, cotton broad cloth, various woven fabrics made of a semisynthetic fiber, such as, broad cloths made of regenerated cellulose fiber, e.g. viscose rayon, cuprammonium rayon or Fortisan, various woven fabrics made of a synthetic fiber, such as, broad cloths made of polyamide (nylon), polyethylene teraphthalate or polyacrylonitrile, and blended yarn woven fabrics of a natural fiber with a semisynthetic fiber or synthetic fiber, such as, broad cloth made of the blended yarn of silk fiber and polyethylene terephthalate fiber. As the examples of the knitted fabric usable as the air barrier layer, there are various knitted fabrics made of the same fiber or twist yarn thereof as the fiber usable for the production of the aforementioned woven fabrics. As examples of the fine net material usable as the air barrier layer, there are various fine nets and fine meshes made of a synthetic fiber or yarn, such as polyamide (nylon), polyethylene terephthalate, polyacrylonitrile, polyethylene, polypropylene or polyvinyl chloride. The thickness of the above woven fabric, knitted fabric and fine net material is usually in the range of about 30 to 300 μm. The void content of the woven fabric, knitted fabric and fine net material is usually about 20 to 60%, preferably about 40 to 60.

In the above air barrier layer composed of the porous material having continuous pores, there is a possibility that liquid components, particularly those containing interfering materials, such as, alkaline materials, pass the inner space of the barrier layer by capillary phenomena. Therefore, it is preferred that the air barrier layer has a hydrophobic property or water repellency to the degree not to generate capillary flow by capillary phenomena. When the hydrophobic property or water repellency of the porous material having continous pores is weak, it is preferable to conduct a treatment to render it hydrophobic or water-repellent. The treatment to render the porous material hydrophobic or water-repellent can be conducted by using a common agent used for hydrophobic treatment or a common water repellent, represented by silicone resin, silicone oil, fluorine contained resin and fluorine contained oil as it is or optionally diluted with a solvent, such as, hexane, cyclohexane or petroleum ether in a solid content of about 0.1 to 5 wt. %, and applying it onto at least one surface in the neighborhood of the porous material having continuous pores by immersing, coating or spraying.

The air barrier is formed by adhering the porous material having continuous pores to the aforementioned organic solvent-soluble binder polymer or water-soluble binder polymer or water-soluble binder polymer composing the matrix of the indicator layer. The above adhesion of the porous material can be conducted by adhering the porous material to the indicator layer when it is in a wet state, and then drying. The indicator layer in a wet state means that the binder polymer composing the matrix of the indicator layer is in a wet state, dispersed state or solution state by the solvent used for dissolving the binder polymer which still remains on wetting the dried membrane with a soluble solvent, such as an organic solvent or water. When the binder polymer of the indicator layer is adhesive, such as, polyvinyl acetate, the porous material having continuous pores can be adhered to the indicator layer by pressing without wetting the indicator layer.

The polymer barrier layer is preferably composed of a hydrophobic or less hydrophilic polymer. Examples or the hydrophobic or less hydrophilic polymer are cellulose acetate propionate, cellulose acetate butyrate, polycarbonate of bisphenol A, polyethylene, polypropylene, ethylene-vinyl acetate copolymer, polyurethane, polystyrene, polyvinyl chloride, vinyl chloride-vinyl acetate copolymer, polyamide (nylon), polymethyl methacrylate and polyvinyl butyral. These polymers may be blended with each other.

The thickness of the polymer barrier layer is usually in the range of about 0.1 to about 6 $\mu$m, preferably about of 0.2 to about 3 $\mu$m. The polymer barrier layer can be provided by applying a polymer organic solvent solution and then drying, according to the method disclosed in Japanese Patent KOKOKU No. 58-19062 or Japanese Patent KOKAI No. 60-21452.

Preferable barriers are air barrier layer of the membrane filter composed of a vinyl polymer, such as, polyethylene or polypropylene or a fluorine-containing vinyl polymer, such as, polytetrafluoroethylene, treated with or without a water repellent, in view of short analytical operation time, high sensitivity and uniform coloring or discoloration of the indicator layer.

The reagent layer is provided on the barrier layer directly or through an adhesive intermediate layer described later. The reagent layer usually contains, in the case of the analytical element for the determination of an ammonia-producing substance, a reagent reacting with the ammonia-producing substance to produce ammonia which is generally an enzyme or a reagent containing an enzyme, an alkaline buffer for releasing the ammonia produced through the reaction as gaseous ammonia efficiently and a hydrophilic polymer binder having a film-forming ability. In the case of the analytical element for the determination of ammonia, the above reagent for producing ammonia is not necessary.

The reagent reacting with an ammonia-producing substance to produce ammonia is preferably an enzyme or a reagent containing an enzyme, and the enzyme suitable for the analysis can be selected according to the kind of the ammonia-producing substance which is the analyte. In the case of using an enzyme as the above reagent, the combination of ammonia-producing substance and reagent is decided by the specificity of the enzyme. Examples of ammonia-producing substance/reagent are urea/urease, creatinine/creatinine deiminase, amino acid/amino acid dehydrogenase, amino acid/amino acid oxidase, amino acid/ammonia lyase, amine/amine oxidase, diamine/amine oxidase, glucose and phosphoamidate/phosphoamidate hexose phosphotransferase, ADP/carbamate kinase and carbamoylphosphate, acid amide/amide hydrolase, nucleobase/nucleobase deaminase, nucleoside/nucleoside deaminase, nucleotide/nucleotide deaminase, guanine/guanase, etc.

The alkaline buffer usable for the reagent layer is usually in the range of pH 7.0 to 12.0, preferably 7.5 to 11.5. Examples of the buffer are ethylenediaminetetraacetic acid (EDTA), tris(hydroxymethyl)aminomethane (Tris), phosphate buffer, N,N-bis(2-hydroxyethyl)glycine (Bicine), N-[tris(hydroxymethyl)methyl]-3-aminopropanesulfuric acid (Taps), N-2-hydroxyethyl-piperazine-N'-2-hydroxypropane-3-sulfonic acid (Heppso), N-2-hydroxyethylpiperazine-N'3-propane sulfonic acid (Epps), N,N-bis(2-hydroxyethyl)-2-aminoethane sulfonic acid, 3-[N-bis(hydroxyethyl)amino]-2-hydroxypropanesulfonic acid (Dipso), N-hydrosyethylpiperazine-N'-ethanesulfonic acid (Hepes), piperazine-N,N'-bis(2-hydroxypropanesulfonic acid) dehydrate (Popso), 3-[N-tris(hydroxymethyl)methylamino]-2-hydroxypropanesulfonic acid (Tapso), N-tris(hydroxymethyl) methylaminoethanesulfonic acid (Tes), N-[2-hydroxy-1,1-bis(hydroxymethyl)ethyl]glycine (Tricine) and the like, their alkali metal salts, such as, lithium salts sodium salts and potassium salts, their alkaline earth metal salts, alkali metal salts of tetraboric acid, such as, sodium tetraborate, disodium carbonate-sodium hydrogen carbonate, and the like. The details of the above buffers are described in Biochemistry, 5, 467–477 (1966). Analytical Biochemistry, 104, 300–310 (1980), The Chemical Society of Japan, "Kagaku-Benran, Kiso-Hen (Chemical Handbook, Fundamental Volume)", 1312–1320, Maruzen, Tokyo (1966), etc.

The hydrophilic polymer binder having a film-forming ability usable for the reagent layer is preferably a binder which substantially does not contain ammonia, which substantially does not generate ammonia at a pH of not less than about 9.0 (pH value $\geq$ 9.0) and of which the binder ability substantially does not vary at a pH of not less than about 9.0.

The about pH 9.0 means the pH where $NH_4^+$ can be sufficiently converted to $NH_3$ ($NH_4^+ \rightarrow NH_3$; pKa=9.2). That the binder ability substantially does not vary at a pH of not less than about 9.0 means that, even when a solution containing the binder is left for a long period in the circumstance of a pH of not less than about 9.0, the viscosity scarsely varies, e.g. at pH 10.0 at 45° C. after 24 hours, the viscosity variation is not more than 1%.

The hydrophilic polymer binder can be selected from the polymers having hydrophilic property among the aforementioned water-soluble binder polymers usable for the indicator layer. Other hydrophilic polymers usable for the reagent layer are gelatin, gelatin derivatives, agarose, pullulan, pullulan derivatives, hydroxyalkyl celluloses, alkyl celluloses, polyvinyl alcohol, polyacrylamide, etc. Among these polymers, hydroxyalkyl celluloses are, in general, preferred.

The reagent layer can contain optionally a wetting agent, a binder crosslinking agent (curing agent), a stabilizer, a heavy metal ion trapping agent (chelating agent), and the like, in addition to the reagent reacting with an ammonia-producing substance to produce ammonia, the alkaline buffer and the hydrophilic polymer binder having a film-forming ability. The heavy metal ion trapping agent is used for masking the heavy metal ion which inhibits enzyme activity. Examples of the heavy metal ion trapping agent are complexanes, such as, EDTA.2Na, EDTA.4Na, nitrilotriacetic acid (NTA) and diethylenetriaminepentaacetic acid.

The reagent layer can be formed by preparing a coating solution by mixing the reagent reacting with an ammonia-producing substance to produce ammonia, the alkaline buffer and the above optional reagents with the hydrophilic polymer binder having a film-forming ability, such as a hydroxyalkyl cellulose, polyvinyl alcohol or agarose, and applying it onto the barrier layer or an adhesive intermediate layer followed by drying.

The amount of the reagent reacting with an ammonia-producing substance to produce ammonia contained in the reagent layer is usually about 0.1 to 50 wt. %, preferably about 0.2 to 20 wt. % of the weight of the polymer binder. A suitable amount of the alkaline buffer is in the range of 1.0 to 50 wt. % of the weight of the polymer binder. In the case of using the heavy metal ion trapping agent, a suitable amount is about 0.5 to 20 wt. % of the weight of the polymer binder. The dry thickness of the reagent layer is usually in the range of 1 to 30 $\mu$m, preferably 2 to 20 $\mu$m.

The adhesive intermediate layer which can be provided between the barrier layer and the reagent layer is composed of a polymer composition which exhibits adhesive property in the atmosphere at a humidity of 10 to 85% at a usual environmental temperature (about 0° to 400° C.). The above adhesive intermediate layer can be provided acording to the materials and method described in Japnese Patent KOKAI No. 60-21452. The polymer composition forming the adhesive intermediate layer is a mixture composed of one or more kinds of a known polymer having a glass transition point (Tg) of not higher than 0° C. and an optional tackfier and an optional surfactant and the like. The thickness of the adhesive intermediate layer is usually in the range of about 0.1 to 6 μm, preferably 1 to 4 μm.

As the example of the polymer usable for the adhesive intermediate layer, there are vinyl acetate-butylacrylate copolymer, poly(ethylacrylate), styrene-butylacrylate-acrylic acid-N-(hydroxymethyl)acrylamide quaternary copolymer, butylacrylate-(ethylacetacetate)methacrylate-2-acrylamide-2-methylpropanesulfonic acid ternary copolymer, and the like.

When the barrier layer is the polymer barrier layer which is a homogeneous nonporous thin layer of a hydrophobic or less hydrophilic polymer, it is preferable to provide the ahesive intermediate layer.

On the reagent layer, it is preferable to provide an ammonia diffusion-preventing layer which has an ability to substantially prevent (or hinder) the ammonia generated in the reagent layer from diffusing into the ammonia-trapping layer described later and which substantially does not conduct trapping of ammonia and ammonia-producing reaction.

The ammonia diffusion-preventing layer may be replaced by another layer having a different function which substantially does not conduct trapping of ammonia and ammonia-producing reaction. The layer having a different function includes a hardened (or crosslinked) hydrophilic polymer layer, a light blocking layer and an adhesive layer.

The polymer binder usable for the ammonia diffusion-preventing layer can be selected arbitrarily from those having a film-forming ability, the film being preferably substantially nonporous and water-permeable and capable of being recoated onto the reagent layer directly or through a suitable intermediate layer. Among the aforementioned polymer binders usable for the indicator layer or the reagent layer, those capable of substantially passing water can be used for this layer. Preferred polymer binders are the hydrophilic polymers used for the reagent layer, and the hydrophilic polymers swelling with water or being water-soluble are particularly preferred. Preferred hydrophilic polymers are hydroxyalkyl celluloses, agarose, polyvinyl alcohol and the like.

The ammonia diffusion-preventing layer may be formed of a polymer binder alone, but it is preferred to control the pH value between about 7.0 to 12.0 by adding a suitable buffer, in order to improve the efficiency for hindering ammonia diffusion. Particularly preferable pH value is in the range of about 8.0 to 11.0.

The buffering ability for maintaining the pH value of the ammonia diffusion-preventing layer in the above range may be any one having a buffering ability in the above pH range. As examples of the buffer usable for hindering ammonia diffusion, there are alkaline buffers and alkaline agents similar to those usable for the aforementioned reagent layer.

The ammonia diffusion-preventing layer is preferably thick in view of hindering ammonia diffusion, whereas it is preferably thin in view of water permeation. Therefore, a suitable thickness is selected so as to satisfy both functions.

The ammonia diffusion-preventing layer is, in the case of a substantially nonporous layer containing a hydrophilic polymer binder, in a thickness of about 2 to 50 μm, preferably about 4 to 30 μm, and the coating amount of the polymer binder is about 1.5 to 40 g, preferably about 3.0 to 25 g per 1 $m^2$ of the analytical element.

In the case of the analytical element for the determination of an ammonia-producing substance, it is preferable to provide an endogeneous ammonia-trapping layer containing a reagent acting on the ammonia already present in an aqueous liquid sample (endogeneous ammonia) to convert it to a state where it is substantially impossible for the ammonia to reach the aforementioned reagent layer, on the ammonia diffusion-preventing layer directly or through a light blocking layer or another intermediate layer. The endogeneous ammonia-trapping layer has a function of trapping the coexisting endogeneous ammonia, prior to the occurrence of the reaction producing ammonia by reaction of the analyte of an ammonia-producing substance, such as, creatinine or urea nitrogen, to the reagent layer.

To trap the endogeneous ammonia means that the reagent system contained in the endogeneous ammonia-trapping layer is bound to render the endogeneous ammonia in a substantially unreleasable state through the analytical operations, or that the reagent system contained in the endogeneous ammonia-trapping layer reacts with the endogeneous ammonia to convert it to another chemical substance, actually a chemical substance different from ammonium salt, ammonium ion and gaseous ammonia, to fix the endogeneous ammonia to the endogeneous ammonia-trapping layer, and thereby, substantially inhibits the endogeneous ammonia to reach the reagent layer. The endogeneous ammonia-trapping layer preferably contains the latter reagent system having a function to react with the endogeneous ammonia to fix it. In this specification, the reagent system reacting with an endogeneous ammonia to convert it to another chemical substance is called an endogeneous ammonia-trapping reagent.

As the endogeneous ammonia-trapping reagent, the reagent compositions containing an enzyme having a catalytic ability acting on ammonia as a substrate to convert it to another substance are preferred. Examples of the endogeneous ammonia-trapping reagent are reagent compositions containing NADH (nicotinamide adenine dinucleotide in reduced form) and/or NADPH (nicotinamide adenine dinucleotide phosphate in reduced form), glutamate dehydrogenase (EC 1.4.1.3;GlDH) and α-ketoglutaric acid or its sodium salt (α-KG). Reagent compositions containing aspartase (EC 4.3.1.1) and fumaric acid or a fumarate salt may also be usable. In the integral multilayer analytical element of the invention, it is preferable to use a reagent composition containing NADH, GlDH and α-KG as the endogeneous ammonia-trapping reagent. In the case of using a reagent composition containing GlDM or a reagent composition containing aspartase, it is preferable to use a suitable buffer so as to maintain the pH value of the endogeneous ammonia-trapping layer to usually not higher than 10.0, preferably in the range of 7.0 to 9.5.

As the buffer for maintaining the above pH value usable for the endogeneous ammonia-trapping reagent, there are the buffers described in The Chemical Society of Japan, "Kagaku-Benran, Kiso-Hen (Chemical Handbook, Fundamental Volume)", 1312–1320, Maruzen, Tokyo (1966), the buffers described in Norman E. Good, et al, Biochemistry, 5 (2), 467–477 (1966), Hydrogen Ion Buffers for Biological Research, the buffers described in R. M. G. Davson et al, Date for Biochemical Research, Second Edition, 476–508, Oxford at the Clarendon Press (1919), the buffers described in Analytical Biochemistry, 104, 300–310 (1980), etc. Besides, organic acids and their alkali metal or alkaline earth metal salt usable for the integral multilayer analytical element described in Japanese Patent KOKOKU No. 57-28277, base polymers acid polymers, alkali metal or or alkaline earth metal salts of the acid polymers usable for the integral multilayer analytical element described in Japanese Patent KOKAI Nos. 59-143959 or 60-10171 and mixtures thereof are also usable as the above buffer.

Among the above pH buffers, examples of particulary preferable ones are a combination of disodium hydrogen phosphate, 3-morpholinoprepanesulfonic acid (MOPS, CAS Reg. No. [1132-61-2]) and sodium hydroxide, a combination of potassium dihydrogen phosphate and disodium hydrogen phosphate, a combination of disodium hydrogen phosphate and citric acid, a combination of boric acid, sodium chloride and borax, a combination of potassium dihydrogen phosphate and sodium tetraborate and the like.

The endogeneous ammonia-trapping layer is composed of reagents, such as, the above endogeneous ammonia-trapping reagent and the pH buffer and a hydrophilic polymer binder having a film-forming ability. As the hydrophilic polymer binder, the same hydrophilic polymer binder usable for the reagent layer can be used. Preferable hydrophilic polymer binders are, in general, gelatin, gelatin derivatives, hydroxyalkyl celluloses, polyvinyl alcohol and agarose.

The thickness of the endogeneous ammonia-trapping layer is usually about 1 to 30 μm, preferably about 2 to 10 μm.

The endogeneous ammonia-trapping layer preferably contains NADPH or NADH, -KG and GlDH. A preferred content (per 1 m² of the endogeneous ammonia-trapping layer) of these components is described below.

|  | Content ( /m²) |
| --- | --- |
| NADPH or NADH | 80–7,000 mg |
| α-KG | 100–10,000 mg |
| GlDH | 2,000–100,000 units |

In the case that the endogeneous ammonia-trapping layer contains aspartase and fumaric acid or fumarate, the content of aspartase is not less than 1,000 units/m², and the content of fumaric acid and/or fumarate is not less than 200 mg/m².

The endogeneous ammonia-trapping layer may be a microporous layer containing the ammonia-trapping reagent, the pH buffer and optional hydrophilic polymer provided in the porous spreading layer or between the porous spreading layer and the ammonia diffusion-hindering layer, as well as the substantially nonporous layer containing the polymer binder provided on the ammonia diffusion-hindering layer as mentioned previously. In the embodiment that the porous spreading layer contains the ammonia-trapping reagents, the spreading layer functions also as the endogeneous ammonia-trapping layer. In the microporous ammonia-trapping layer, the content (coating amount) of the ammonia-trapping reagent, the kind, content (coating amount) and pH range of the pH buffer and the like are substantially the same as the case of the nonporous layer. The adhesion of the endogeneous ammonia-trapping layer to the porous spreading layer is preferably conducted according to the adhesion technics of porous materials described in Japanese Patent KOKAI No. 61(1986)-4959(EP 0 166 365 A).

In the case of the analytical element for the determination of ammonia, it is a matter of course that the endogeneous ammonia-trapping layer is not provided.

A light-blocking layer may be provided beween the barrier layer and the endogeneous ammonia-trapping layer. The light-blocking layer is water-transmissive or water-permeable, and light-shielding particulates or particulates having both functions of light-shielding and light-reflecting are dispersed in and held by a small amount of a hydrophilic or weakly hydrophilic polymer binder having a film-forming ability. The light-blocking layer shields the color of an aqueous liquid sample, particularly the red color of hemoglobin in a whole blood sample, spotted on the spreading layer during measuring the detectable change which occurred in the indicator layer, such as, color change or color buffer, from the side of the light-transmissive support. This layer may also fuction as a light-reflecting layer or a background layer.

Examples of particulates having both functions of light-shielding and light-reflecting are titanium dioxide particulates, barium sulfate particulates, aluminum particulates and microflakes, and the like.

As the examples of the hydrophilic or weakly hydrophilic polymer binder having a film-forming ability, there are gelatin, gelatin derivatives, hydroxyalkyl cellulose, agarose, polyvinyl alcohol and the like. A known curing agent (crosslinking agent) may be blended with gelatin or gelatin derivatives.

The volume ratio of light-blocking particulates to hydrophilic polymer binder in the dry state is 10: about 2.5 to about 7.5, preferably about 3.0 to about 6.5. When the light-blocking particulates are titanium dioxide particulates, the ratio by weight of polymer binder is about 0.6 to about 1.8, preferably about 0.8 to 1.5 per 10 of titanium dioxide. The thickness of the light-blocking layer in the dry state is about 3 μm to about 30 μm, preferably about 5 μm to about 20 μm.

The porous spreading layer may be a woven fabric spreading layer disclosed in U.S. Pat. No. 4,292,272, U.S. Pat. No. 4,783,315, etc., such as, plain weaves including broad cloth and poplin, a knitted fabric spreading layer disclosed in EP 0 162 302 A, etc., such as tricot, double tricot or milanese, the spreading layer made of organic polymer fiber pulp-containing paper disclosed in Japanese Patent KOKAI No. 57-148250, a nonfibrous isotropic porous spreading layer, such as, a membrane filter (blushed polymer layer) disclosed in U.S. Pat. No. 3,992,158, a continuous microspaces-containing porous layers where polymer particulates, glass particulates or diatomaceous earth are dispersed in a hydrophilic polymer binder, or a continuous microspaces-containing porous layer where polymer particulates are joined so as to contact with each other at a point by using a polymer adhesive which does not swell in water (three-dimensional lattice structure layer), or the like.

The porous spreading layer may function as the endogeneous ammonia-trapping layer by incorporating the ammonia-trapping reagent, pH buffer, etc. In this case, preferred spreading layers are fibrous spreading layers represented by woven fabric spreading layers and knitted fabric spreading layers in view that the reagent composition is easily incorporated therein.

An example of the method of incorporating the reagent composition containing the ammonia-trapping enzyme into the spreading layer is comprised of providing a porous spreading layer on a coating layer and then applying an aqueous solution or organic solvent-containing solution containing the reagent composition containing the enzyme onto the spreading layer, as disclosed in EP 0 119 861 A, EP 0 162 302 A, EP 0 162 301 A, etc.

Physical activation treatment represented by glow discharge or corona discharge disclosed in U.S. Pat. No. 4,783,315 may be provided on at least one side of the woven fabric or knitted fabric used as the porous spreading layer. The woven fabric or knitted fabric may be treated with degreasing by washing with water, or impregnating with a hydrophilic polymer. By providing the fabric with one or more of the above treatments, the fabric is rendered hydrophilic, and the adhesive force to the layer located on the underside, i.e. near the support, can be increased.

Although the endogeneous ammonia-trapping layer which is substantially nonporous and contains a hydrophilic polymer binder can function as an adhesive layer for joining the porous spreading layer directly without providing an adhesive layer separately, a known adhesive layer which is formed of a hydrophilic polymer represented by gelatin may be provided for the purpose of joining the spreading layer tightly. The thickness of the adhesive layer in a dry state is in the range of about 0.5 $\mu$m to 5 $\mu$m.

A surfactant may be incorporated in the indicator layer, the reagent layer, the ammonia diffusion-hindering layer, the endogeneous ammonia-trapping layer, the light-reflecting layer, the adhesive layer, the spreading layer containing or not containing the ammonia-trapping reagent composition, etc. A suitable surfactant is a nonionic surfactant, such as, p-octylphenoxypolyethyoxyethanol, p-nonylphenoxypolyethoxyethanol, polyoxyethylene oleyl ether, polyoxyethylenesorbitanmonolaurate, p-nonylphenoxypolyglycidol, octylglucoside, etc. The spreading action (metering action) for spreading an aqueous liquid sample is improved by adding a nonionic surfactant to the spreading layer. The water in an aqueous liquid sample is easily substantially uniformly absorbed by the reagent layer or a water absorption layer by adding a nonionic surfactant to these layers during analytical operations, and the liquid contact with the spreading layer becomes rapid and substantially uniform.

The multilayer analytical element of the invention can be prepared according to a known method disclosed in the specifications of the foregoing patents.

In view of manufacturing, packaging, transportation, storage, measuring operations, etc., the multilayer analytical element of the invention is preferably cut into square or circular pieces having a side or diameter of about 15 mm to about 30 mm, and put in a slide frame as disclosed in Jaapnese Patent KOKAI No. 57-63452, U.S. Pat. No. 4,169,751, U.S. Pat. No. 4,387,990, PCT application WO 83/00391, etc. for use. According to the object of use, the element may be put in a cassette or a magazine in the form of a strip, may be adhered to or put in a card having an opening, or the like.

The analysis of the analyte (ammonia-producing substance) in a liquid sample using the analytical element of the invention can be conducted according to the operations disclosed in the specifications of the foregoing patents. That is, about 5 $\mu$l to about 30 $\mu$l, preferably about 8 $\mu$l to about 15 $\mu$l of a drop of an aqueous liquid sample, such as, whole blood, blood plasma, blood serum or urine, is spotted onto the spreading layer, and incubated at a substantially constant temperature in the range of about 20° C. to about 400° C., preferably around 370° C., for 1 minute to 10 minutes. Then, the coloring or discoloration occurred in the element is measured by reflection photometry using a visible or ultraviolet light having a miximum absorption wave length or the vicinity thereof from the side of the light-transmissive support, and the content of the analyte in the liquid sample is determined by the principle of colorimetry using a calibration curve which was previously prepared. Alternatively, the fluorescence intensity emitted from the element is measured, and the content of the analyte in the liquid sample is determined by using a calibration curve which was previously prepared. By fixing the amount of the spotted liquid sample, incubation time and temperature, the quantitative analysis of an analyte can be conducted at a high accuracy. When the chemical analyzer disclosed in Japanese Patent KOKAI Nos. 60-125543, 60-220862, 61-294367, 58-161867, etc. is used, the quantitative analysis can be conducted by very simple operations at a high accuracy.

The analytical element of the invention is characterized by the binder polymer of the indicator layer and the polymer of the undercoat layer of the support, and the effects of the invention can be obtained by employing one of them.

The conventional element using the latex of vinyl acetate-acrylate ester copolymer as the binder for the indicator has problems of insufficient sensitivity, uneven coating due to the precipitation because of latex, unsuitable for the system using a pH indicator because of the occurrence of pH variation. However, all of the above problems can be resolved by employing a polyvinylalkyl ether as the binder.

On the other hand, in general, gelatin was undercoated onto the support of conventional element. When the indicator layer of the polyvinylalkyl ether is incorporated, a very small amount of ammonia contained in the gelatin is detected due to the improved sensitiity, and affects the background optical density adversely. Then, a binder polymer not containing ammonia is substituted for the gelatin undercoating for improving the adhesion of the indicator layer, and as a result, the background optical density is lowered. The measuring accuracy is further improved by the stabilization of the base line.

EXAMPLES

EXAMPLE 1

The following undercoat layer was coated onto a colorless transparent polyethylene terephthalate (PET) film having a thickness of 180 $\mu$m, and dried.

| Undercoat Layer | |
|---|---|
| Gelatin | 0.07 g/m² |
| p-Chlorophenol | 0.7 g/m² |

On the undercoat layer, the following indicator layer was applyed in a form of an ethanol solution, and dried.

| Indicator Layer | |
|---|---|
| Bromophenol Blue | 140 mg/m² |
| Polyvinyl ethyl ether | 2.1 g/m² |
| (Weight average molecular weight: about 40,000) | |
| Sodium hydroxide | 200 mg/m² |

Subsequently, on the indicator layer, a membrane filter made of polyethylene having a mean pore size of 0.2 μm, a void content of 75% and a thickness of 100 μm was uniformly pressed to provide an air barrier layer. On the air barrier layer, the following reagent layer was applied in a form of an aqueous solution, and dried.

| Reagent Layer | |
|---|---|
| Hydroxyethyl cellulose | 16 g/m² |
| (Mean molecular weight: about 40,000) | |
| Mean substitution degree of hydroxyethyl group: | 1.0–1.3 |
| Average number of moles: | 1.8–2.5 |
| Sodium tetraborate | 4 g/m² |
| pH of the coating solution: | 10.0 |

The above reagent layer was almost uniformly wetted with 0.2% p-nonylphenoxypolyglycidol aqueous solution. Immediately, a knitted fabric (gauge number: 40, 25% weight loss by aqueous NaOH solution treatment) was superposed onto the reagent layer, and laminated uniformly by passing between press rolls.

An ethanol solution of the following polyvinylpyrrolidon was impregnated into the laminate by applying for the purpose of improving spreading property, and dried to complete an integral multilayer analytical element for the determination of ammonia.

| Polyvinylpyrrolidone | 7.76 g/m² |
|---|---|
| (Mean molecular weight: about 1,200,000) | |

EXAMPLE 2

The following undercoat layer was coated onto a colorless transparent PET film having a thickness of 180 μm, and dried.

| Undercoat Layer | |
|---|---|
| Polyvinyl methyl ether | 0.035 g/m² |
| (Weight average molecular weight: about 40,000) | |
| p-Chlorophenol | 0.7 g/m² |

On the undercoat layer, the following indicator layer was applied in a form of an aqueous solution, and dried.

| Indicator Layer | |
|---|---|
| Bromophenol Blue | 340 mg/m² |
| Vinyl acetate-ethylacrylate copolymer latex | 8.5 g/m² |
| N-Polyoxyethylene-N-octanesulfonamide | 100 mg/m² |

Subsequently, on the indicator layer, a membrane filter made of polyethylene having a mean pore size of 0.2 μm, a void content of 75% and a thickness of 100 μm was uniformly pressed to provide an air barrier layer. On the air barrier layer, the following reagent layer was applied in a form of an aqueous solution, and dried.

| Reagent Layer | |
|---|---|
| Hydroxyethyl cellulose | 16 g/m² |
| (Mean molecular weight: about 40,000) | |
| Mean substitution degree of hydroxyethyl group: | 1.0–1.3 |
| Average number of moles: | 1.8–2.5 |
| Sodium tetraborate | 4 g/m² |
| pH of the coating solution: | 10.0 |

The above reagent layer was almost uniformly wetted with 0.2% p-nonylphenoxypolyglycidol aqueous solution. Immediately, a knitted fabric (gauge number: 40, 25% weight loss by aqueous NaOH solution treatment) was superposed onto the reagent layer, and laminated uniformly by passing between press rolls.

An ethanol solution of the following polyvinylpyrrolidone was impregnated into the laminate by applying for the purpose of improving spreading property, and dried to complete an integral multilayer analytical element for the determination of ammonia.

| Polyvinylpyrrolidone | 7.76 g/m² |
|---|---|
| (Mean molecular weight: about 1,200,000) | |

EXAMPLE 3

The following undercoat layer was coated onto a colorless transparent PET film having a thickness of 180 μm, and dried.

| Undercoat Layer | |
|---|---|
| Polystyrene | 0.035 g/m² |
| p-Chlorophenol | 0.7 g/m² |

On the undercoat layer, the following indicator layer was applyed in a form of an ethanol solution, and dried.

| Indicator Layer | |
|---|---|
| Bromophenol Blue | 340 mg/m² |
| Vinyl acetate-ethylacrylate copolyer latex | 8.5 g/m² |
| N-Polyoxyethylene-N-octanesulfonamide | 100 mg/m² |

Subsequently, on the indicator layer, a membrane filter made of polyethylene having a mean pore size of 0.2 μm, a void content of 75% and a thickness of 100 μm was uniformly pressed to provide an air barrier layer. On the air barrier layer, the following reagent layer was applied in a form of an aqueous solution, and dried.

| Regent Layer | |
|---|---|
| Hydroxyethyl cellulose<br>(Mean molecular weight: about 40,000) | 16 g/m$^2$ |
| Mean substitution degree of hydroxyethyl group: | 1.0–1.3 |
| Average number of moles: | 1.8–2.5 |
| Sodium tetraborate | 4 g/m$^2$ |
| pH of the coating solution: | 10.0 |

The above reagent layer was almost uniformly wetted with 0.2% p-nonylphenoxypolyglycidol aqueous solution. Immediately, a knitted fabric (gauge number: 40, 25% weight loss by aqueous NaOH solution treatment) was superposed onto the reagent layer, and laminated uniformly by passing between press rolls.

An ethanol solution of the following polyvinylpyrrolidon was impregnated into the laminate by applying for the purpose of improving spreading property, and dried to complete an integral multilayer analytical element for the determination of ammonia.

| | |
|---|---|
| Polyvinylpyrrolidone<br>(Mean molecular weight: about 1,200,000) | 7.76 g/m$^2$ |

EXAMPLE 4

The following undercoat layer was coated onto a colorless transparent PET film having a thickness of 180 μm, and dried.

| Undercoat Layer | |
|---|---|
| Polyvinyl methyl ether<br>(Weight average molecular weight: about 40,000) | 0.035 g/m$^2$ |
| p-Chlorophenol | 0.7 g/m$^2$ |

On the undercoat layer, the following indicator layer was applyed in a form of an ethanol solution, and dried.

| Indicator Layer | |
|---|---|
| Bromophenol Blue | 140 mg/m$^2$ |
| Polyvinyl ethyl ether | 2.1 g/m$^2$ |
| Sodium hydroxide | 200 mg/m$^2$ |

Subsequently, on the indicator layer, a membrane filter made of polyethylene having a mean pore size of 0.2 μm, a void content of 75% and a thickness of 100 μm was uniformly pressed to provide an air barrier layer. On the air barrier layer, the following reagent layer was applied in a form of an aqueous solution, and dried.

| Reagent Layer | |
|---|---|
| Hydroxyethyl cellulose<br>(Mean molecular weight: about 40,000) | 16 g/m$^2$ |
| Mean substitution degree of hydroxyethyl group: 1.0–1.3<br>Average number of moles: 1.8–2.5 | |
| Sodium tetraborate | 4 g/m$^2$ |
| pH of the coating solution: | 10.0 |

The above reagent layer was almost uniformly wetted with 0.2% p-nonylphenoxypolyglycidol aqueous solution. Immediately, a knitted fabric (gauge number: 40, 25% weight loss by aqueous NaOH solution treatment) was superposed onto the reagent layer, and laminated uniformly by passing between press rolls.

An ethanol solution of the following polyvinylpyrrolidon was impregnated into the laminate by applying for the purpose of improving spreading property, and dried to complete an integral multilayer analytical element for the determination of ammonia.

| | |
|---|---|
| Polyvinylpyrrolidone<br>(Mean molecular weight: about 1,200,000) | 7.76 g/m$^2$ |

COMPARATIVE EXAMPLE 1

An integral multilayer analytical element for the determination of ammonia was prepared similar to Example 1, except that the indicator layer was changed to the following layer.

| Indicator Layer | |
|---|---|
| Bromophenol Blue | 340 mg/m$^2$ |
| Vinyl acetate-ethylacrylate copolyme latex | 8.5 g/m$^2$ |
| N-Polyoxyethylene-N-octanesulfonamide | 100 mg/m$^2$ |

Evaluation of Quantitative Ability for Ammonia Determination

The integral multilayer analytical elements for the determination of ammonia of Examples 1 to 4 and Comparative Example 1 were evaluated by the following method.

Whole blood samples for the evaluation test were prepared by adding ammonium sulfate to a human whole blood so that the final concentration became about 50, 100, 150, 200, 250, 500 μg/dl. 10 μl of demineralized distilled water or the whole blood sample for the evaluation test was spotted onto the spreading layer of each analytical element, and coloring optical density after 6 minutes was measured at 600 nm by the reflection photometry. Moreover, a calibration curve was prepared by using the above optical density values and the values obtained by measuring respective whole blood samples for the evaluation test by the glutamate dehydrogenase (GlDH) method. Besides, the above coloring test was repeated ten times as to each analytical element, and respective optical densities were measured. Each optical density was converted to ammonia concentration by using the above calibration curve, and variation coefficients were determined. The results of the analytical elements of Examples 1 and 4 and Comparative Example 1 are shown in Table 1, and the results of the analytical elements of Examples 2, 3, 4 and Comparative Example 1 are shown in Table 2.

As shown in Table 1, the coloring optical densities of the analytical elements of Examples 1 and 4 are higher than those of Comparative Example 1 were the polymer in the indicator layer is different, and moreover, the measuring accuracy is also improved.

As shown in Table 2, the reflection optical densities (background coloring optical density) of the analytical elements of Examples 2–4 obtained by spotting demineralized distilled water are lower than those of Comparative Example 1 where the undercoating of the support is gelatin, and moreover, the measuring accuracy is also improved.

TABLE 1

| Ammonia Conc. (μg/dl) | Analytical Element | | | | | |
|---|---|---|---|---|---|---|
| | Example 1 | | Example 4 | | Comparative 1 | |
| | Optical Density (OD) | Variation Coeff. (CV) | Optical Density (OD) | Variation Coeff. (CV) | Optical Density (OD) | Variation Coeff. (CV) |
| 0 | 0.32 | — | 0.14 | — | 0.32 | — |
| 52 | 0.45 | 6.4 | 0.30 | 4.4 | 0.34 | 17.4 |
| 87 | 0.52 | 4.0 | 0.37 | 2.8 | 0.41 | 9.8 |
| 134 | 0.65 | 2.4 | 0.49 | 2.1 | 0.51 | 7.5 |
| 186 | 0.72 | 1.5 | 0.58 | 1.6 | 0.60 | 6.0 |
| 233 | 0.85 | 2.3 | 0.65 | 1.0 | 0.66 | 5.1 |
| 484 | 1.11 | 2.0 | 1.02 | 1.6 | 0.92 | 4.7 |

TABLE 2

| Ammonia Conc. (μg/dl) | Analytical Element | | | | | | | |
|---|---|---|---|---|---|---|---|---|
| | Example 2 | | Example 3 | | Example 4 | | Comparative 1 | |
| | OD | CV | OD | CV | OD | CV | OD | CV |
| 0 | 0.12 | — | 0.20 | — | 0.14 | — | 0.32 | — |
| 52 | 0.22 | 6.8 | 0.28 | 4.8 | 0.30 | 4.4 | 0.34 | 17.4 |
| 87 | 0.34 | 5.2 | 0.33 | 3.0 | 0.37 | 2.8 | 0.41 | 9.8 |
| 134 | 0.43 | 4.1 | 0.44 | 1.9 | 0.49 | 2.1 | 0.51 | 7.5 |
| 186 | 0.51 | 3.5 | 0.52 | 2.2 | 0.58 | 1.6 | 0.60 | 6.0 |
| 233 | 0.62 | 3.2 | 0.60 | 3.3 | 0.65 | 1.0 | 0.66 | 5.1 |
| 484 | 0.95 | 2.5 | 0.96 | 2.2 | 1.02 | 1.6 | 0.92 | 4.7 |

EXAMPLE 5

The following undercoat layer was coated onto a colorless transparent polyethylene terephthalate (PET) film having a thickness of 180 μm, and dried.

| Undercoat Layer | |
|---|---|
| Gelatin | 0.07 g/m² |
| p-Chlorophenol | 0.7 g/m² |

On the undercoat layer, the following indicator layer was applyed in a form of an ethanol solution, and dried.

| Indicator Layer | |
|---|---|
| Bromophenol Blue | 140 mg/m² |
| Polyvinyl ethyl ether (Weight average molecular weight: about 40,000) | 2.1 g/m² |
| Sodium hydroxide | 200 mg/m² |

Subsequently, on the indicator layer, a membrane filter made of polyethylene having a mean pore size of 0.2 μm, a void content of 75% and a thickness of 100 μm was uniformly pressed to provide an air barrier layer. On the air barrier layer, the following reagent layer, the intermediate layer and the endogeneous ammonia-trapping layers were successively applied in a form of an aqueous solution, and dried.

| Reagent Layer | |
|---|---|
| Alkali treated gelatin | 11.7 g/m² |
| Sodium tetraborate | 1.7 g/m² |
| p-Nonylphenoxypolyglycidol (Glycidol units: 10 on average) | 300 mg/m² |
| Creatinine iminohydrolase (EC 3.5.4.21) | 750 U/m² |
| pH of the coating solution: 8.0 | |
| Ammonia Diffusion-Hindering Layer | |
| Alkali-treated gelatin | 8.3 g/m² |
| Sodium tetraborate | 750 mg/m² |
| p-Nonylphenoxypolyglycidol | 200 mg/m² |
| (Glycidol units: 10 on average) | |
| pH of the coating solution: 9.0 | |
| Endogeneous Ammonia-Trapping Layer | |
| Alkali-treated gelatin | 7.5 g/m² |
| Sodium tetraborate | 1.35 g/m² |
| p-Nolylphenoxypolyglycidol (Glycidol units: 10 on average) | 170 mg/m² |
| α-Ketoglutaric acid | 2.5 g/m² |
| NADPH | 1.6 g/m² |
| Glutamate dehydrogenase | 70,000 U/m² |
| pH of the coating solution: 8.0 | |

The above endogeneous ammonia-trapping layer was almost uniformly wetted with 0.2% p-nonylphenoxypolyglycidol aqueous solution. Immediately, a knitted fabric (gauge number: 40, 25% weight loss by aqueous NaOH solution treatment) was superposed onto the reagent layer, and laminated uniformly by passing between press rolls.

An ethanol solution of the following polyvinylpyrrolidon was impregnated into the laminate by applying for the purpose of improving spreading property, and dried to complete an integral multilayer analytical element for the determination of creatinine.

| Polyvinylpyrrolidone (Mean moleculr weight: about 1,200,000) | 7.76 g/m² |
|---|---|

EXAMPLE 6

The following undercoat layer was coated onto a colorless transparent PET film having a thickness of 180 μm, and dried.

| Undercoat Layer | |
|---|---|
| Polyvinyl methyl ether (Weight average molecular weight: about 40,000) | 0.035 g/m² |
| p-Chlorophenol | 0.7 g/m² |

On the undercoat layer, the following indicator layer was applyed, and dried.

| Indicator Layer | |
|---|---|
| Bromophenol Blue | 340 mg/m² |
| Vinyl acetate-ethylacrylate copolymer latex | 8.5 g/m² |
| N-Polyoxyethylene-N-octanesulfonamide | 100 mg/m² |

Subsequently, on the indicator layer, a membrane filter made of polyethylene having a mean pore size of 0.2 μm, a void content of 75% and a thickness of 100 μm was uniformly pressed to provide an air barrier layer. On the air barrier layer, the following reagent layer, the intermediate layer and the endogeneous ammonia-trapping layers were successively applied in a form of an aqueous solution, and dried.

| Reagent Layer | |
|---|---|
| Alkali-treated gelatin | 11.7 g/m² |
| Sodium tetraborate | 1.7 g/m² |
| p-Nonylphenoxypolyglycidol (Glycidol units: 10 on average) | 300 mg/m² |
| Creatinine iminohydrolase (EC 3.5.4.21) | 750 U/m² |
| pH of the coating solution: 8.0 | |
| Ammonia Diffusion-Hindering Layer | |
| Alkali-treated gelatin | 8.3 g/m² |
| Sodium tetraborate | 750 mg/m² |

| | |
|---|---|
| p-Nonylphenoxypolyglycidol | 200 mg/m² |
| (Glycidol units: 10 on average) | |
| pH of the coating solution: 9.0 | |
| Endogeneous Ammonia-Trapping Layer | |
| Alkali-treated gelatin | 7.5 g/m² |
| Sodium tetraborate | 1.35 g/m² |
| p-Nolylphenoxypolyglycidol | 170 mg/m² |
| (Glycidol units: 10 on average) | |
| α-Ketoglutaric acid | 2.5 g/m² |
| NADPH | 1.6 g/m² |
| Glutamate dehydrogenase | 70,000 U/m² |
| pH of the coating solution: 8.0 | |

The above endogeneous ammonia-trapping layer was almost uniformly wetted with 0.2% p-nonylphenoxypolyglycidol aqueous solution. Immediately, a knitted fabric (gauge number: 40, 25% weight loss by aqueous NaOH solution treatment) was superposed onto the reagent layer, and laminated uniformly by passing between press rolls.

An ethanol solution of the following polyvinylpyrrolidon was impregnated into the laminate by applying for the purpose of improving spreading property, and dried to complete an integral multilayer analytical element for the determination of creatinine.

| | |
|---|---|
| Polyvinylpyrrolidone | 7.76 g/m² |
| (Mean molecular weight: about 1,200,000) | |

EXAMPLE 7

The following undercoat layer was coated onto a colorless transparent PET film having a thickness of 180 μm, and dried.

| Undercoat Layer | |
|---|---|
| Polystyrene | 0.035 g/m² |
| p-Chlorophenol | 0.7 g/m² |

On the undercoat layer, the following indicator layer was applyed in a form of an ethanol solution, and dried.

| Indicator Layer | |
|---|---|
| Bromophenol Blue | 340 mg/m² |
| Vinyl acetate-ethylacrylate copolymer latex | 8.5 g/m² |
| N-Polyoxyethylene-N-octanesulfonamide | 100 mg/m² |

Subsequently, on the indicator layer, a membrane filter made of polyethylene having a mean pore size of 0.2 μm, a void content of 75% and a thickness of 100 μm was uniformly pressed to provide an air barrier layer. On the air barrier layer, the following reagent layer, the intermediate layer and the endogeneous ammonia-trapping layers were successively applied in a form of an aqueous solution, and dried.

| Reagent Layer | |
|---|---|
| Alkali-treated gelatin | 11.7 g/m² |
| Sodium tetraborate | 1.7 g/m² |
| p-Nonylphenoxypolyglycidol | 300 mg/m² |
| (Glycidol units: 10 on average) | |
| Creatinine iminohydrolase | 750 U/m² |
| (EC 3.5.4.21) | |
| pH of the coating solution: 8.0 | |

| Ammonia Diffusion-Hindering Layer | |
|---|---|
| Alkali-treated gelatin | 8.3 g/m² |
| Sodium tetraborate | 750 mg/m² |
| p-Nonylphenoxypolyglycidol | 200 mg/m² |
| (Glycidol units: 10 on average) | |
| pH of the coating solution: 9.0 | |
| Endogeneous Ammonia-Trapping Layer | |
| Alkali-treated gelatin | 7.5 g/m² |
| Sodium tetraborate | 1.35 g/m² |
| p-Nolylphenoxypolyglycidol | 170 mg/m² |
| (Glycidol units: 10 on average) | |
| α-Ketoglutaric acid | 2.5 g/m² |
| NADPH | 1.6 g/m² |
| Glutamate dehydrogenase | 70,000 U/m² |
| pH of the coating solution: 8.0 | |

The above endogeneous ammonia-trapping layer was almost uniformly wetted with 0.2% p-nonylphenoxypolyglycidol aqueous solution. Immediately, a knitted fabric (gauge number: 40, 25% weight loss by aqueous NaOH solution treatment) was superposed onto the reagent layer, and laminated uniformly by passing between press rolls.

An ethanol solution of the following polyvinylpyrrolidon was impregnated into the laminate by applying for the purpose of improving spreading property, and dried to complete an integral multilayer analytical element for the determination of creatinine.

| | |
|---|---|
| Polyvinylpyrrolidone | 7.76 g/m² |
| (Mean molecular weight: about 1,200,000) | |

EXAMPLE 8

The following undercoat layer was coated onto a colorless transparent PET film having a thickness of 180 μm, and dried.

| Undercoat Layer | |
|---|---|
| Polyvinyl methyl ether | 0.035 g/m² |
| (Weight average molecular weight: about 40,000) | |
| p-Chlorophenol | 0.7 g/m² |

On the undercoat layer, the following indicator layer was applyed, and dried.

| Indicator Layer | |
|---|---|
| Bromophenol Blue | 140 mg/m² |
| Polyvinyl ethyl ether | 2.1 g/m² |
| (Weight average molecular weight: about 40,000) | |
| Sodium hydroxide | 200 mg/m² |

Subsequently, on the indicator layer, a membrane filter made of polyethylene having a mean pore size of 0.2 μm, a void content of 75% and a thickness of 100 μm was uniformly pressed to provide an air barrier layer. On the air barrier layer, the following reagent layer, the intermediate layer and the endogeneous ammonia-trapping layers were successively applied in a form of an aqueous solution, and dried.

| Reagent Layer | |
|---|---|
| Alkali-treated gelatin | 11.7 g/m² |
| Sodium tetraborate | 1.7 g/m² |
| p-Nonylphenoxypolyglycidol | 300 mg/m² |
| (Glycidol units: 10 on average) | |

-continued

| | |
|---|---|
| Creatinine iminohydrolase (EC 3.5.4.21) | 750 U/m² |
| pH of the coating solution: 8.0 | |
| Ammonia Diffusion-Hindering Layer | |
| Alkali-treated gelatin | 8.3 g/m² |
| Sodium tetraborate | 750 mg/m² |
| p-Nonylphenoxypolyglycidol (Glycidol units: 10 on average) | 200 mg/m² |
| pH of the coating solution: 9.0 | |
| Endogeneous Ammonia-Trapping Layer | |
| Alkali-treated gelatin | 7.5 g/m² |
| Sodium tetraborate | 1.35 g/m² |
| p-Nolylphenoxypolyglycidol (Glycidol units: 10 on average) | 170 mg/m² |
| α-Ketoglutaric acid | 2.5 g/m2 |
| NADPH | 1.6 g/m² |
| Glutamate dehydrogenase | 70,000 U/m² |
| pH of the coating solution: 8.0 | |

The above endogeneous ammonia-trapping layer was almost uniformly wetted with 0.2% p-nonylphenoxypolyglycidol aqueous solution. Immediately, a knitted fabric (gauge number: 40, 25% weight loss by aqueous NaOH solution treatment) was superposed onto the reagent layer, and laminated uniformly by passing between press rolls.

An ethanol solution of the following polyvinylpyrrolidon was impregnated into the laminate by applying for the purpose of improving spreading property, and dried to complete an integral multilayer analytical element for the determination of creatinine.

| | |
|---|---|
| Polyvinylpyrrolidone (Mean molecular weight: about 1,200,000) | 7.76 g/m² |

COMPARATIVE EXAMPLE 2

An integral multilayer analytical element for the determination of creatinine was prepared similar to Example 5, except that the indicator layer was changed to the following layer.

| Indicator Layer | |
|---|---|
| Bromophenol Blue | 340 mg/m² |
| Vinyl acetate-ethylacrylate copolymer latex | 8.5 g/m² |
| N-Polyoxyethylene-N-octanesulfonamide | 100 mg/m² |

Evaluation of Quantitative Ability for Creatinine Determination

The integral multilayer analytical elements for the determination of ammonia of Examples 5 to 8 and Comparative Example 2 were evaluated by the following method.

Whole blood samples for the evaluation test were prepared by adding creatinine to a human whole blood so that the final concentration became about 1.0, 4.0, 11.0 μg/dl. 10 μl of demineralized distilled water or the whole blood sample for the evaluation test was spotted onto the spreading layer of each analytical element, and coloring optical density after 6 minutes was measured at 600 nm by the reflection photometry. Moreover, a calibration curve was prepared by using the above optical density values and the values obtained by measuring respective whole blood samples for the evaluation test by the Jaffé method. Besides, the above coloring test was repeated ten times as to each analytical element, and respective optical densities were measured. Each optical density was converted to creatinine concentration by using the above calibration curve, and variation coeffcients were determined. The results of the analytical elements of Examples 5 and 8 and Comparative Example 2 are shown in Table 3, and the results of the analytical elements of examples 6, 7, 8 and Comprarative Example 2 are shown in Table 4.

As shown in Table 3, the coloring optical densities of the analytical elements of Examples 5 and 8 are higher than those of Comparative Example 2 where the polymer in the indicator layer is different, and moreover, the measuring accuracy is also improved.

As shown in Table 4, the reflection optical densities (background coloring optical density) of the analytical elements of Examples 6–8 obtained by spotting demineralized distilled water are lower than those of Comprative Example 2 where the undercoating of the support is gelatin, and moreover, the measuring accuracy is also improved.

TABLE 3

| | Analytical Element | | | | | |
|---|---|---|---|---|---|---|
| Creatinine Conc. (mg/dl) | Example 5 | | Example 8 | | Comparative 2 | |
| | Optical Density (OD) | Variation Coeff. (CV) | Optical Density (OD) | Variation Coeff. (CV) | Optical Density (OD) | Variation Coeff. (CV) |
| 0 | 0.28 | — | 0.16 | — | 0.32 | — |
| 1.2 | 0.51 | 0.7 | 0.39 | 0.6 | 0.40 | 6.8 |
| 4.1 | 0.76 | 0.6 | 0.64 | 0.5 | 0.58 | 6.2 |
| 10.9 | 1.10 | 0.8 | 1.02 | 0.6 | 0.81 | 4.2 |

TABLE 4

| Creatinine Conc. (mg/dl) | Analytical Element | | | | | | | |
|---|---|---|---|---|---|---|---|---|
| | Example 6 | | Example 7 | | Example 8 | | Comprative 1 | |
| | OD | CV | OD | CV | OD | CV | OD | CV |
| 0 | 0.12 | — | 0.20 | — | 0.16 | — | 0.32 | — |
| 1.2 | 0.30 | 2.0 | 0.36 | 1.8 | 0.39 | 0.6 | 0.40 | 6.8 |
| 4.1 | 0.48 | 1.3 | 0.60 | 1.6 | 0.64 | 0.5 | 0.58 | 6.2 |
| 10.9 | 0.76 | 1.6 | 1.00 | 0.8 | 1.02 | 0.6 | 0.81 | 4.2 |

We claim:

1. In an integral multilayer analytical element for the determination of ammonia or an ammonia-producing substance comprising a light-transmissive liquid-impermeable support, an indicator layer containing an indicator which produces a detectable change by gaseous ammonia, a liquid permeation barrier layer, a reagent layer containing an alkaline buffer and optionally a reagent capable of reacting with said ammonia-producing substance to produce ammonia, and, a spreading layer, laminated in this order, the improvement which comprises that the indicator layer contains a polyvinyl alkyl ether as a binder polymer.

2. The analytical element of claim 1 wherein said polyvinyl alkyl ether is a member selected from the group consisting of polyvinyl methyl ether, polyvinyl ethyl ether and polyvinyl isobutyl ether.

3. In an integral multilayer analytical element for the determination of ammonia or an ammonia-producing substance comprising a light-transmissive liquid-impermeable support, an indicator layer containing an indicator which produces a detectable change by gaseous ammonia, a liquid permeation barrier layer, a reagent layer containing an alkaline buffer and optionally a reagent capable of reacting with said ammonia-producing substance to produce ammonia and a spreading layer laminated in this order, the improvement which comprises that the surface of said support facing toward the indicator layer is undercoated with a polymer selected from the group consisting of a polyvinyl alkyl ether, a hydroxyalkyl cellulose, an alkyl cellulose, polystyrene, a polyalkyl methacrylate, polyvinylidene chloride, polyvinyl alcohol and polyvinyl pyrrolidone.

4. The analytical element of claim 1 wherein the surface of said support facing toward the indicator layer is undercoated with a polymer selected from the group consisting of a polyvinyl alkyl ether, a hydroxyalkyl cellulose, an alkyl cellulose, polystyrene, a polyalkyl methacrylate, polyvinylidene chloride, polyvinyl alcohol and polyvinyl pyrrolidone.

5. The analytical element of claim 3 or 4 wherein said surface is undercoated with polyvinyl alkyl ether.

6. The analytical element of claim 5 wherein said polyvinyl alkyl ether is a member selected from the group consisting of polyvinyl methyl ether, polyvinyl ethyl ether and polyvinyl isobutyl ether.

7. The analytical element of claim 1, 3 or 4 wherein said liquid permeation barrier layer is an air barrier layer composed of a porous material having continuous voids.

8. The analytical element of claim 7 wherein said porous material is a membrane filter made of a material selected from the group consisting of polyethylene, polypropylene and polytetrafluoroethylene.

9. The analytical element of claim 1, 3, or 4, which further comprises an ammonia diffusion-preventing layer comprising a polymer binder placed on the reagent layer.

10. The analytical element of claim 9 wherein said polymer binder is selected from the group consisting of hydroxyalkyl cellulose, agarose and polyvinyl alcohol.

11. The analytical element of claim 9 which is for the determination of an ammonia-producing substance and further comprises an endogeneous ammonia-trapping layer containing a reagent composition containing an enzyme of which the substrate is ammonia.

12. The analytical element of claim 1 wherein the indicator contains 1 to 2% by weight of the binder polymer.

13. The analytical element of claim 3 wherein the indicating layer is coated with 5 to 500 mg/m$^2$ of the polymer.

14. In an integral multilayer analytical element for the determination of ammonia or an ammonia-producing substance consisting essentially of a light-transmissive liquid-impermeable support, an indicator layer containing an indicator which produces a detectable change by gaseous ammonia, a liquid permeation barrier layer, a reagent layer containing an alkaline buffer and optionally a reagent capable of reacting with said ammonia-producing substance to produce ammonia, and, a spreading layer, laminated in this order, the improvement which comprises that the indicator layer contains a polyvinyl alkyl ether as a binder polymer.

* * * * *